US00PP34232P2

(12) United States Plant Patent
Bedard

(10) Patent No.: US PP34,232 P2
(45) Date of Patent: May 17, 2022

(54) FLORIBUNDA ROSE PLANT NAMED 'WEKWIBSCRYPER'

(50) Latin Name: *Rosa hybrida*
Varietal Denomination: WEKwibscryper

(71) Applicant: Early Morning LLC, Lawrenceburg, IN (US)

(72) Inventor: Christian Bedard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 17/300,878

(22) Filed: Dec. 3, 2021

(51) Int. Cl.
*A01H 6/74* (2018.01)
*A01H 5/02* (2018.01)

(52) U.S. Cl.
USPC ..... Plt./141

(58) Field of Classification Search
USPC ..... Plt./141
See application file for complete search history.

(56) References Cited

U.S. PATENT DOCUMENTS

PP4,671 P 3/1981 Delbard
PP5,975 P 5/1987 Moore
PP6,262 P 8/1988 Stephens et al.
PP6,714 P 4/1989 Christensen et al.
PP10,072 P 10/1997 Carruth
PP11,562 P 10/2000 Zary
PP20,744 P2 2/2010 Zary

OTHER PUBLICATIONS

Prior Product Sales, 1 page, Mar. 8, 2021.

"Rosa Soulieana—Trees and Shrubs Online", https://treesandshrubsonline.org/articles/rosa/rosa-soulieana/, 4 pages, last visited Dec. 17, 2021.

Rosa 'International Herald Tribune' (Rose 'International Herald Tribune'), shootgardening.co.uk, https://www.shootgardening.co.uk/plant/rosa-international-herald-tribune, 4 pages, last visited Dec. 17, 2021.

Rose (Rosa 'Dr. Huey') in the Roses Database, Garden.org., https://garden.org/plants/view/1545/Rose-Rosa-Dr-Huey/, 9 pages, last visited Dec. 15, 2021.

Weeks Roses Wholesale Rose Catalog, "Sweet Madame Blue," 13 pages, 2022.

*Primary Examiner* — Annette H Para
(74) *Attorney, Agent, or Firm* — McKee, Voorhees & Sease, PLC

(57) ABSTRACT

A new variety of Floribunda rose suitable for garden decoration, having flowers of lavender with magenta center coloration.

1 Drawing Sheet

Classification: The present invention relates to a new *Rosa hybrida* plant.

Variety denomination: The new plant has the varietal denomination 'WEKwibscryper'.

BACKGROUND OF THE INVENTION

This invention relates to a new and distinct variety of Floribunda Rose. It has a non-disseminated seedling of my creation as its seed parent with the following genetic origin {[(International Herald Tribune x *Rosa soulieana* derivative) x (Sweet Chariot x Blue Nile)] x [Blueberry Hill x Stephen's Big Purple]} and a non-disseminated seedling of my creation as its pollen parent with the following genetic origin (Crystalline x Perfume Perfection).

SUMMARY OF THE INVENTION

Among the features which distinguish the new variety from other presently available and commercial rose cultivars known to the inventor are the following combinations of characteristics: its unique lavender with magenta center flower coloration, its strong citrus-like to spicy fragrance and its excellent color stability throughout the life of the flower. The plant has a rounded bushy moderately spreading growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'WEKwibscryper' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, a non-disseminated seedling of my creation by the following combination of characteristics: whereas 'WEKwibscryper' bears very double flowers (about 43 to 75 petals) of lavender with magenta center coloration, the non-disseminated seedling bears double flowers of red-purple with a lavender eye coloration with significantly lesser petalage (about 27 to 38 petals). The new variety has a rounded bushy moderately spreading medium height growing habit (about 92 to about 140 cm. in height), whereas the seed parent has a rounded bushy and compact significantly shorter growing habit (about 70 to about 85 cm. in height).

The new variety may be distinguished from its pollen parent, a non-disseminated seedling of my creation by the following combination of characteristics: whereas 'WEKwibscryper' bears very double flowers (about 43 to 75 petals) of lavender with magenta center coloration, the non-disseminated seedling bears double flowers of soft lavender coloration with significantly lesser petalage (about 25 to 35 petals). The new variety bears medium sized flowers (about 7.0 to about 10.2 cm. in diameter), whereas the pollen parent bears smaller flowers (about 6.5 to about 8.0 cm. in diameter).

COMPARISON WITH THE CLOSEST COMMERCIALLY AVAILABLE CULTIVAR

The new variety may be distinguished from its closest commercially available cultivar, 'JACperby' (U.S. Plant Pat. No. 20,744) by the following combination of characteristics: whereas 'WEKwibscryper' bears very double flowers (about 43 to 75 petals) of lavender with magenta center coloration, 'JACperby' bears double flowers of lavender coloration with significantly lesser petalage (about 20 to 25 petals). The new variety has a rounded bushy moderately spreading medium height growing habit (about 92 to about 140 cm. in height), whereas the closest commercially available cultivar has a significantly shorter growing habit (about 80 to about 100 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Rancho Cucamonga, Calif. in the month of November. Phenotypic expression may vary with environmental, cultural and climatic conditions, as well as differences in conditions of light and soil.

FLOWER

The new variety sometimes bears its flowers singly, sometimes in clusters of two to seven per stem. Flowers may be borne in regular rounded clusters on strong somewhat short to medium length stems (about 18 to about 62 cm.). The cluster ranges from about 14.5 to about 22.0 cm. in diameter. Outdoors, the plant blooms abundantly and nearly continuously during the growing season. The flowers have a strong citrus-like to spicy fragrance.

BUD

The peduncle is about 2.1 to about 6.6 cm. in length, of average caliper (about 0.2 to about 0.3 cm. in diameter), and usually erect. It is moderately rough, with few stipitate glands, and few hairs. Peduncle color is between 146C and 146B sometimes lightly suffused, especially on the side exposed to the sun, with between 187B and 187C.

Before the calyx breaks, the bud is about 1.2 to about 1.9 cm. in diameter at the widest point, about 1.3 to about 1.9 cm. in length, and pointed to somewhat ovoid in shape. The surface of the bud bears between 10 to 12 foliaceous appendages, very few stipitate glands and many hairs, usually with slender entire foliaceous parts extending beyond the tip of the bud about ¾ or more of its length. Bud color is between 138A and 146C.

The sepals are 5 per flower, about 2.2 to about 4.2 cm. in length and about 0.7 to about 1.1 cm. in width at the widest point. The outer surface color of the sepal is between 138A and 146C. The outer surface of the sepal is somewhat rough and bears between 0 to 5 foliaceous appendages with very few stipitate glands, and many hairs. The inner surface color of the sepal is near 146D broadly bordered by near 137C. After the sepals open, the inner surface color is often moderately suffused, especially on the area exposed to the sun, with between 187B and 187C. The inner surface of the sepal is covered with fine wooly tomentum; sepal margins are entire and lined with some stipitate glands and many hairs. The sepals are moderately permanent, usually straight in shape with acute apices.

The receptacle of the flower is of short length (about 0.3 to about 0.7 cm.) and moderately thin in caliper (about 0.6 to about 0.8 cm. in diameter). The receptacle is cup-shaped in form. Its surface is smooth with some hairs and with moderately thick fleshy walls. The receptacle color is between 144A and 146C.

As the petals open (after the calyx breaks), the bud is about 1.7 to about 2.4 cm. in diameter at the widest point, about 2.0 to about 2.8 cm. in length, and ovoid to somewhat globular in form. The color of the under surfaces of the newly opened petals is between 59B and 61A. At the point where the petal attaches, there is a large zone of between 154D and 150D. The color of the upper surfaces of the newly opened petals is near 80C at the lower third of the petal suffusing to between 61A and 64A on the remaining surface of the petal. At the point where the petal attaches, there is a moderately large zone of between 154D and 150D.

BLOOM

When fully open, the bloom ranges from about 7.0 to about 10.2 cm. in diameter. Petalage is very double with about 43 to 75 petals and about 3 to 15 petaloids irregularly arranged. When partially open, the bloom form is moderately high centered to cupped, and the petals are tightly spiraled to cupped with petal edges moderately reflexed outward. When fully open, the bloom form is more cupped, and the petals are loosely cupped with petal edges moderately reflexed outward.

PETALS

The substance of the petals is moderately heavy and of somewhat thin to medium thickness, with upper surfaces slightly shiny to moderately satiny and under surfaces moderately shiny. The petals are about 3.4 to about 5.3 cm. in length and about 2.4 to about 5.0 cm. in width at the widest point. Petal margins are entire.

The outer petals are moderately obovate to somewhat rounded in shape with rounded apices and sometimes slightly notched with one notch.

The inner petals are broadly obovate in shape with rounded apices.

Petaloids are about 2.6 to about 3.6 cm. in length and about 1.2 to about 2.5 cm. in width at the widest point. Petaloids are irregularly shaped somewhat obovate to moderately oblanceolate with rounded to sometimes lacerated apices.

NEWLY OPENED FLOWER

The under surface color of the outer petals is between 69B and 76C at the lower third of the petal suffusing to between 78D and 74D on the remaining surface of the petal and often moderately suffused with between 71B and 74B. At the point where the petal attaches, there is a small zone of between 9D and 11C. The upper surface color of the outer petals is between 69B and 76C at the lower third of the petal suffusing to between 72C and 71C on the remaining surface of the petal. At the point where the petal attaches, there is a small zone of between 9D and 11C.

The under and upper surface color of the intermediate and inner petals is between 69B and 76C at the lower third of the petal suffusing to between 61B and 67A on the remaining surface of the petal.

The under and upper surface colors of the petaloids are similar in coloration to the upper and under surfaces of the intermediate and inner petals.

The general tonality of the newly opened flower is between 61B and 67A.

THREE-DAY-OLD FLOWER

The under surface color of the outer petals is between 76C and 76B. At the point where the petal attaches, there is a large zone of between 155A and 155C. The upper surface color of the outer petals is between 81D and 80D. At the point where the petal attaches, there is a large zone of between 155A and 155C.

The under surface color of the intermediate and inner petals is between 73B and 72D. The upper surface color of the intermediate and inner petals is between 70B and 72D.

The under and upper surface colors of the petaloids are similar in coloration to the upper and under surfaces of the intermediate and inner petals.

The general tonality of the three-day-old flower is between 70B and 72D.

On the spent bloom, the petals usually drop off cleanly.

In November in Rancho Cucamonga, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 75) and are arranged regularly about the pistils; a few are mixed with petaloids. The filaments are of short to medium length (about 0.3 to about 0.7 cm.) most with anthers. Filaments are between 18D and 8D in color sometimes lightly suffused with between 60B and 60C. The anthers are moderately small for the class and all open approximately at the same time. Anther color when immature is near 21B on the external part and near 4D on the internal part. Anther color at maturity is near 164C on the external part and near 200A on the internal part. Pollen is moderately abundant and between 18C and 19C in color.

FEMALE REPRODUCTIVE ORGANS

Pistils vary in number (average about 75). The styles are moderately even, somewhat short to average in length (about 0.4 to about 0.7 cm.), moderately thin in caliper, and loosely bunched to somewhat separated. Stigma color is between 16D and 14D. Style color is between 154D and 1D usually heavily suffused with between 60A and 59B. Ovaries are usually all enclosed in the calyx. The ovaries are of medium size and between 158A and 159C in color.

Hips have not been observed on this variety when grown in Rancho Cucamonga, Calif.

FOLIAGE

The compound leaves are usually comprised of three to seven leaflets and are borne abundantly. The seven-leaflet leaves are about 7.0 to about 19.0 cm. in length and about 5.5 to about 14.8 cm. in width at the widest point, moderately leathery to somewhat crisp in texture on both sides, and glossy in finish on the upper side and semi-glossy in finish on the under side. The leaves have a pinnate venation pattern. The terminal leaflets are about 3.1 to about 9.1 cm. in length and about 2.3 to about 5.6 cm. in width at the widest point, shaped broadly ovate to somewhat oval with acute apices and rounded to somewhat acute bases. Their margins are usually simply serrate.

The upper surface color of the mature leaf is between 139A and 147A. The under surface color of the mature leaf is between 137C and 147C. The under and upper colors of the leaf veins on the mature leaf are similar in coloration to the upper and under surfaces colors of the mature leaf The upper surface color of the young leaf is between 137B and 146C, often lightly suffused with between 187A and 187B. The under surface color of the young leaf is between 146B and 147C, often lightly suffused with between 187B and 187C. The under and upper colors of the leaf veins on the young leaf are similar in coloration to the upper and under surfaces colors of the young leaf The rachis is about 3.4 to about 8.4 cm. in length, about 0.1 to about 0.2 cm in width at the widest point, and rough. The upper side is deeply grooved with very few hairs and few stipitate glands on the edges of the grooves. The under side of the rachis is rough with very few hairs, very few stipitate glands and few small prickles. The rachis color is near 146D on the under side and near 137C on the upper side, often moderately suffused on the young leaves with between 187B and 187C.

The stipules are about 0.6 to about 1.5 cm. in length and of somewhat narrow to medium width (about 0.3 to about 0.8 cm.) with medium to moderately long straight points that usually turn out at an angle of more than 45 degrees and sometimes recurve toward the stem. The under and upper surface color of the stipule is between 137B and 137C often lightly suffused on the young leaves with between 187B and 187C. The upper and under surfaces of the stipules are smooth in texture.

The petiole is somewhat light to average in caliper and rough. The upper side is deeply grooved with very few hairs and few stipitate glands on the edges of the grooves. The under side of the petiole is rough with very few hairs, very few stipitate glands and few small prickles. The petiole is about 0.3 to about 1.6 cm. in length and about 0.1 to about 0.2 cm in width at the widest point. The petiole color is near 146D on the under side and near 137C on the upper side, often moderately suffused on the young leaves with between 187B and 187C.

The plant displays an average degree of resistance to powdery mildew (*Sphaerotheca pannosa*), downy mildew (*Peronospora sparsa*), and rust (*Phragmidium* sp.) as compared to other commercial varieties grown under comparable conditions in Rancho Cucamonga, Calif. The plant's winter hardiness and drought/heat tolerance are yet to be determined.

GROWTH

The plant has a rounded bushy moderately spreading medium height growing habit (about 92 to about 140 cm. in height and about 125 to about 152 cm. spread at the widest point), with very full branching. It displays vigorous growth and the canes are of medium sized to somewhat heavy caliper for the class (about 1.5 to about 2.9 cm. in diameter at the widest point).

The color of the major stems is between 146A and 147B. The major stems are rough in texture and they bear some large prickles that are about 0.8 to about 1.3 cm. in length. The large prickles are angled slightly downward with a moderately short broad oval base; prickle color is between 165B and 164A. The major stem bears few small prickles of similar shape and coloration.

The color of the branches is between 137C and 148B. The branches are rough in texture and they bear few large prickles which are of similar shape to the large prickles on the major stems. The prickles are about 0.5 to about 0.9 cm. in length. Prickle color is between 160C and 160B. The branches bear very few small prickles of similar shape and coloration.

The color of the new shoots is between 146C and 146B often moderately suffused with between 187A and 187B. The new shoots are rough in texture and they bear few large prickles which are of similar size and shape to the large prickles on the branches; prickle color is between 152D and 152C usually heavily suffused with between 187C and 187D. The shoots bear very few small prickles of similar shape and coloration.

I claim:

1. A new and distinct Floribunda rose plant of the variety designated 'WEKwibscryper' substantially as described and illustrated herein.

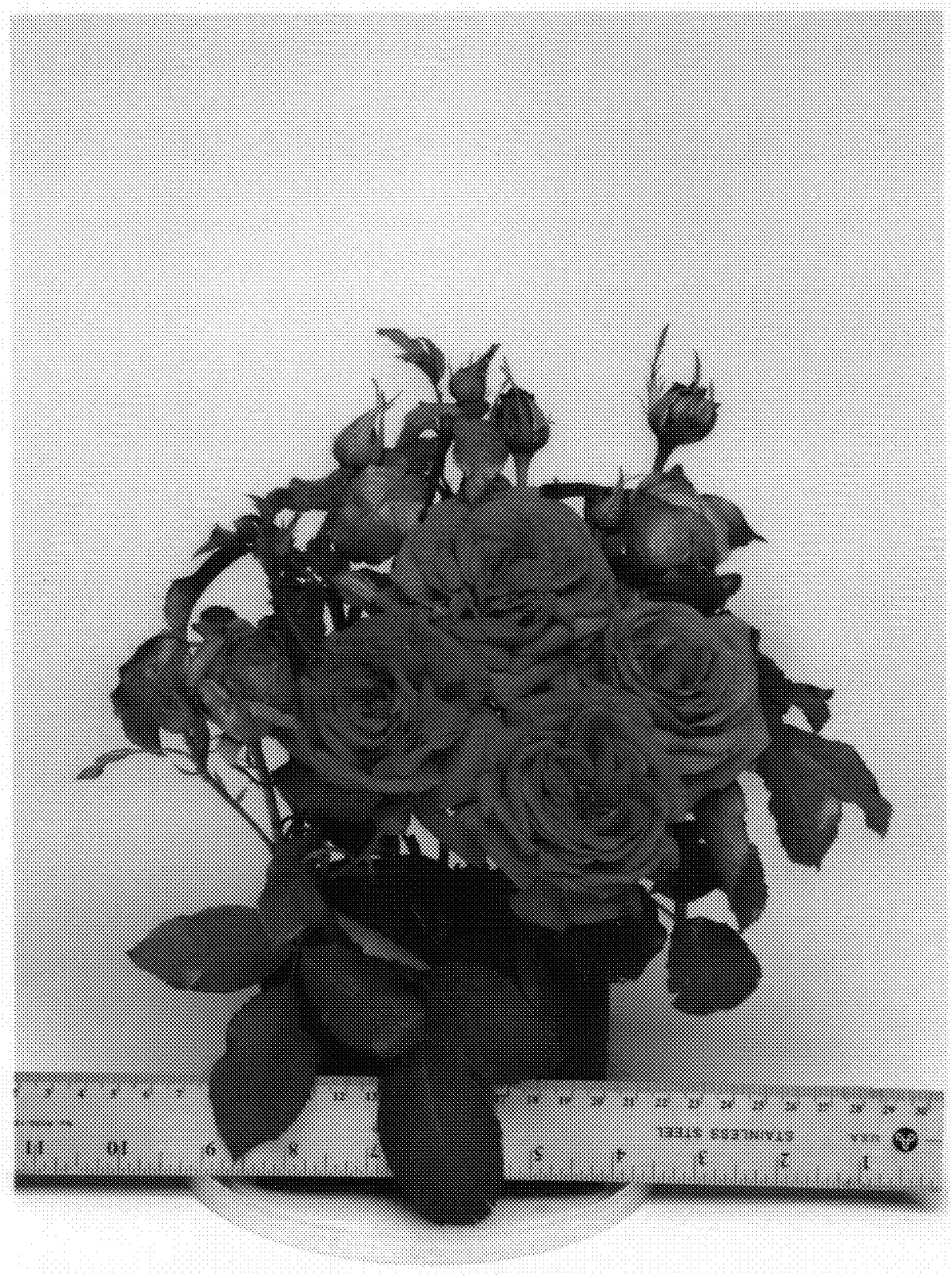

* * * * *